(12) United States Patent
Yokokawa

(10) Patent No.: US 7,521,265 B2
(45) Date of Patent: Apr. 21, 2009

(54) METHOD FOR MEASURING AN AMOUNT OF STRAIN OF A BONDED STRAINED WAFER

(75) Inventor: Isao Yokokawa, Gunma (JP)

(73) Assignee: Shin-Etsu Handotai Co., Ltd., Tokyo (JP)

( * ) Notice: Subject to any disclaimer, the term of this patent is extended or adjusted under 35 U.S.C. 154(b) by 444 days.

(21) Appl. No.: 10/584,771

(22) PCT Filed: Jan. 11, 2005

(86) PCT No.: PCT/JP2005/000165

§ 371 (c)(1),
(2), (4) Date: Jun. 28, 2006

(87) PCT Pub. No.: WO2005/069374

PCT Pub. Date: Jul. 28, 2005

(65) Prior Publication Data

US 2007/0166845 A1 Jul. 19, 2007

(30) Foreign Application Priority Data

Jan. 16, 2004 (JP) ............................. 2004-008744

(51) Int. Cl.
*H01L 21/66* (2006.01)
(52) U.S. Cl. ..................... 438/14; 438/16; 438/18; 438/50; 257/E21.521; 257/E21.53
(58) Field of Classification Search .......... 257/E21.522, 257/E21.53, E21.529
See application file for complete search history.

(56) References Cited

U.S. PATENT DOCUMENTS 5,414,747 A 5/1995 Ruud et al.

2007/0134821 A1* 6/2007 Thakur et al. .............. 438/5

(Continued)

FOREIGN PATENT DOCUMENTS

JP A 01-276052 11/1989

(Continued)

OTHER PUBLICATIONS

M. Erdtmann et al, "Structural Characterization of Strained Silicon Substrates by X-Ray Diffraction and Reflectivity", Extended Abstracts of the 2003 International Conference on Solid State Devices and Material, Tokyo, pp. 290-291, 2003.

(Continued)

*Primary Examiner*—Walter L Lindsay, Jr.
*Assistant Examiner*—Cheung Lee
(74) *Attorney, Agent, or Firm*—Oliff & Berridge, PLC

(57) ABSTRACT

In a method for measuring an amount of strain of a bonded strained wafer, at least one strained layer is formed on a single crystal substrate. The bonded strained wafer is measured with respect to two asymmetric diffraction planes with diffraction plane indices (XYZ) and (−X−YZ) by an X-ray diffraction method, a reciprocal lattice space map is created from the measured data, and the amount of strain of the strained layer is calculated from the peak positions for the respective diffraction planes of the single crystal substrate and the strained layer appearing on the reciprocal lattice space map. Thereby, amounts of strain in the horizontal direction and in the vertical direction of the strained layer can be measured in a shorter time and more simply.

18 Claims, 8 Drawing Sheets

U.S. PATENT DOCUMENTS

2007/0151356 A1 * 7/2007 Sumigawa et al. ............ 73/777

FOREIGN PATENT DOCUMENTS

| JP | A 11-304729 | 11/1999 |
| JP | A 2000-286413 | 10/2000 |
| JP | A 2001-217430 | 8/2001 |
| JP | A 2002-164520 | 6/2002 |
| JP | A 2002-305293 | 10/2002 |
| JP | A 2003-229360 | 8/2003 |
| JP | A 2003-229361 | 8/2003 |

OTHER PUBLICATIONS

W.L. Bond, "Precision Lattice Constant Determination", Acta Crystallographica, pp. 814-818, Oct. 10, 1960.

* cited by examiner (b)

(c)

(a)

(b)

(c)

(a)

(a)

(b)

(a)

(b)

METHOD FOR MEASURING AN AMOUNT OF STRAIN OF A BONDED STRAINED WAFER

TECHNICAL FIELD

The present invention relates to a method for measuring an amount of strain of a bonded strained wafer in which at least one strained layer is formed on a single crystal substrate by a bonding method.

Background Art

A so-called strained Si layer which is a thin-film silicon (Si) single crystal layer to which tensile strain is introduced has attracted attention as material for satisfying demands for high-speed semiconductor devices in recent years because high carrier mobility can be obtained as compared to a normal Si layer with no strain.

The strained Si layer can be obtained, for example, by forming a SiGe layer by epitaxial growth on a Si substrate with crystal plane orientation of (100), furthermore epitaxially growing a Si layer on the SiGe layer, thereby introducing tensile strain to the Si layer by utilizing the characteristic that a lattice constant of the SiGe layer is a little larger than a lattice constant of the Si layer. At this time, for forming a strained Si layer in which sufficient strain is introduced, it is required to form the surface of the SiGe layer with a condition sufficiently lattice-relaxed on which the strained Si layer is formed. In addition, the condition that the SiGe layer is sufficiently lattice-relaxed means that a lattice constant of the SiGe layer is nearly an inherent lattice constant determined according to Ge concentration.

As a method for forming the strained Si layer as described above, as well as a method mainly conducted by the epitaxial method as described above, there has been known a method in which a SiGe layer is formed on a Si substrate to be a bond wafer, the surface of the formed SiGe layer of the bond wafer is bonded with a Si substrate to be a base wafer through an oxide film and thereby a bonded wafer is produced, and then the Si substrate of the bond wafer is thinned to be a strained Si layer as disclosed in Japanese Patent Application Laid-open (kokai) No. 2001-217430 and No. 2002-164520. In this case, as disclosed in Japanese Patent Application Laid-open (kokai) No. 2002-164520, according to the concentration-oxidation method for enhancing Ge concentration by thermal oxidation of the surface of the SiGe layer, a SiGe layer with high Ge concentration can be obtained. In addition, a wafer in which a SiGe layer is formed on an insulator film such as an oxide film is occasionally referred to as SGOI (SiGe On Insulator) wafer.

In this case, the thinning of the Si substrate of a bond wafer is performed by the grinding and polishing method, vapor etching such as PACE (Plasma Assisted Chemical Etching) method, and the ion-implantation delamination method (which is also referred to as smart cut (a registered trademark) method).

Moreover, in Japanese Patent Application Laid-open (kokai) No. 2002-305293, there has been disclosed a method for forming a separating layer by ion implantation in a Si substrate of a bond wafer in which a SiGe layer, a silicon layer, and an insulator layer on the Si substrate, bonding the surface of the insulator layer of the bond wafer with a base wafer, and then delaminating it at the separating layer and thereby making the Si layer of the delaminated layer transferred to the base wafer side a strained Si layer.

On the other hand, when an SGOI wafer is produced, there is a method using SIMOX (Separation by IMplanted OXygen) method in which oxygen ions are implanted from the surface of the SiGe layer and annealing is performed as a method for forming an oxide film layer in an epitaxially-grown SiGe layer.

A lattice relaxation rate is occasionally used as an amount representing degree of lattice relaxation of a SiGe layer. This is an amount representing degree of lattice relaxation relatively with being 0% when a lattice constant of the SiGe layer is the same as the lattice constant of Si and with being 100% when a lattice constant of the SiGe layer is the same as an inherent lattice constant determined by Ge concentration. On the other hand, as an amount representing degree of strain of the strained Si layer, a strain rate is occasionally used. This is an amount representing how much a lattice constant of the strained Si layer extends or diminishes as compared to the lattice constant of Si. Magnitude of such an amount determines carrier mobility of the Strained Si layer. In the present specification, an extending amount is represented by a positive value, and an diminishing amount is represented by a negative value.

And, the X-ray diffraction method using an XRD (X-Ray Diffraction) apparatus is known as a method for evaluating a lattice relaxation rate of a SiGe layer formed on a Si substrate with crystal plane orientation of (100) or a strain rate of a strained Si layer formed on the surface of the SiGe layer.

This is a method for radiating X-ray to a wafer of a measuring subject, capturing a peak position of diffraction signal strength for the Si substrate and a peak position for the SiGe layer (or a peak position for the strained Si layer) obtained from a specified plane (for example, (224), (113), (004), or the like) as a θ–2θ curve or a reciprocal lattice space map, measuring declination from the peak position of the Si substrate in the θ–2θ curve or the reciprocal lattice space map, and thereby calculating a lattice relaxation rate of the SiGe layer (or a strain rate of the strained Si layer).

This method is effective in the case of the wafer produced by using the SIMOX method in which a SiGe layer and a strained Si layer is formed in order from one Si substrate. However, for example, in the case of SSOI (Strained Silicon On Insulator) structure formed using two Si substrates by a bonding method as described in the documents, an accurate lattice relaxation rate (or a strained rate) has not been possible to be obtained. Its reason is as follows.

Crystal orientation of a wafer has declination from a specified value in the range of production tolerance. FIG. 8 is an explanation view showing crystal orientation declination to be generated in a wafer with a crystal plane orientation of (100), (a) is a view seeing a wafer from a direction vertical to a surface thereof and (b) is a view seeing a wafer from a direction parallel to a surface thereof. [001] and [010] represent crystal orientations. As shown, crystal orientation of a wafer has declination from a specified value by a Twist angle due to declination of orientation in a wafer plane and tilts from a specified value by a Tilt angle due to declination of inclination of a wafer plane. A bonded SOI (Silicon On Insulator) wafer produced by bonding two wafers thereof has crystal orientation declination in which respective Twist angles and Tilt angles of the two wafers are synthesized. FIG. 9 is an explanation view showing crystal orientation declination to be generated in a bonded wafer produced by bonding two Si wafers having crystal plane orientation (100) with one wafer being for forming an SOI layer and with the other for a supporting substrate, (a) is a view seeing the wafer from a direction vertical to a surface thereof and (b) is a view seeing the wafer from a direction parallel to a surface thereof. When the bonded SOI wafer is measured by an X-ray diffraction method, diffraction strength peaks of the SOI layer and the Si substrate appear in different positions respectively by effect of Tilt angles and Twist angles although there is no strain in the SOI layer. On the other hand, in the case of a SIMOX wafer, which is produced from one wafer, even if crystal orientation of the substrate has declination from a specified value, an SOI layer is formed by epitaxial growth and therefore the crystal orientations of the SOI layer and the substrate are the same, thereby diffraction strength peak positions for the SOI layer and the substrate correspond to each other.

As explained above, in the case that an amount of strain of a strained Si wafer with a strained Si layer is measured, a diffraction strength peak for the strained Si layer appears in a position deviating from that of the Si substrate because the strained Si layer has strain, therefore an amount of strain can be obtained from the difference of the diffraction strength peaks. However, in the case that a strained Si layer and a Si substrate are produced by a bonding method, diffraction strength peak positions for the strained Si layer appear in positions under the effect of the three of strain, Tilt angle, and Twist angle. Therefore, only an amount of strain cannot be separated and measured and an accurate amount of strain of the strained Si layer cannot be obtained. Therefore, carrier mobility of the produced strained Si layer cannot be evaluated accurately.

Accordingly, Extended Abstracts of the 2003 International Conference on Solid State Devices and Materials, Tokyo, 2003, pp. 290-291 discloses a method for measuring a Tilt angle and a Twist angle in advance, subtracting effect of these declined angles, and calculating a strain rate (a lattice relaxation rate), besides analyzing an amount of strain. However, in this method, measurement of a Tilt angle and a Twist angle is required to be performed in addition, and measurement of a reciprocal lattice space map taking about 8 hours in one time is required to be performed 4 times at intervals of 90°, therefore there is a problem that an extremely long time has to be used on evaluation of a strain rate (a lattice relaxation rate).

Moreover, other than the X-ray diffraction method, by micro-Raman spectroscopy, an amount of strain of a bonded strained wafer can be measured. However, in this method, there is a problem that only an amount of strain in the horizontal (plane) direction can be measured and an amount of strain in the vertical (depth) direction cannot be measured. Moreover, there is a problem that in the case of measuring a lattice relaxation rate of the SiGe layer by micro-Raman spectroscopy, it cannot be measured unless a Ge concentration in the SiGe layer is preliminarily given. As a method for measuring a Ge concentration in the SiGe layer, SIMS (Secondary Ion Mass Spectrometer) and such are exemplified. However, because this is fundamentally a destructive inspection, there is a problem that this method reduces yield of wafers in production.

DISCLOSURE OF THE INVENTION

Accordingly, the present invention was conceived in view of the above problems. An object of the present invention is to provide a method for measuring an amount of strain by which amounts of strain in the horizontal direction and in the vertical direction of the strained layer in a bonded strained wafer can be measured by the X-ray diffraction method in a shorter time and more simply.

In order to accomplish the above object, according to the present invention, there is provided a method for measuring an amount of strain of a bonded strained wafer in which at least one strained layer is formed on a single crystal substrate by a bonding method, wherein at least, the bonded strained wafer is measured with respect to two asymmetric diffraction planes with diffraction plane indices (XYZ) and (−X−YZ) by an X-ray diffraction method, a reciprocal lattice space map is created from the measured data, and the amount of strain of the strained layer is calculated from the peak positions for the respective diffraction planes of the single crystal substrate and the strained layer appearing on the reciprocal lattice space map.

As described above, the bonded strained wafer is measured with respect to two asymmetric diffraction planes with diffraction plane indices (XYZ) and (−X−YZ) by an X-ray diffraction method (hereinafter, occasionally described as (XYZ) diffraction plane and such), and a reciprocal lattice space map is created from the measured data. And, by using the characteristic that position declinations of diffraction strength peaks of the strained layer for the respective diffraction planes which is caused by effect of crystal orientation declination such as a Tilt angle and a Twist angle appear at the same magnitude in the same direction respectively, an amount of strain of the strained layer can be calculated from the relation of the peak positions for the respective diffraction planes of the single crystal substrate and the strained layer appearing on the reciprocal lattice space map. Therefore, amounts of strain in the horizontal direction and in the vertical direction of the strained layer can be measured by two measuring operations according to an X-ray diffraction method, which are less than a conventional method.

In this case, it is preferable that when the amount of strain of the strained layer is calculated, in the case that two peaks for the respective diffraction planes of the single crystal substrate appearing on the reciprocal lattice space map are located at symmetric positions with respect to a vertical axis passing through the origin of the reciprocal lattice space map, the peak positions for the strained layer are moved rotationally and modified in the circumferential direction centering the origin so that the two peak positions for the respective diffraction planes of the same strained layer appearing on the reciprocal lattice space map is located symmetrically with respect to the vertical axis, and thereby the peak positions for the strained layer determined by the amount of strain are obtained.

As described above, when the amount of strain of the strained layer is calculated, in the case that two peaks for the respective diffraction planes of the single crystal substrate appearing on the reciprocal lattice space map are located at symmetric positions with respect to a vertical axis passing through the origin of the reciprocal lattice space map, the axis setting has accurately been conducted at measuring respective diffraction planes. Therefore, the peak positions for the strained layer are moved rotationally and modified in the circumferential direction centering the origin so that the two peak positions for the respective diffraction planes of the same strained layer appearing on the reciprocal lattice space map is located symmetrically with respect to the vertical axis, and thereby the peak positions for the strained layer determined by the amount of strain can be obtained with removing effect of crystal orientation declination due to Tilt, Twist, or the like.

Moreover, it is preferable that in the case that two peaks for the respective diffraction planes of the single crystal substrate are not located at the symmetric positions, in order that the peak of the single crystal substrate for any one of the asymmetric diffraction planes is located at the symmetric position to the peak of the single crystal substrate for the other of the asymmetric diffraction planes, at least the peak position for the strained layer for the said other asymmetric diffraction plane is moved in parallel, and then the peak positions for the strained layer are moved rotationally and modified in the circumferential direction centering the origin so that the two peak positions for the respective diffraction planes of the same strained layer appearing on the reciprocal lattice space map are located at symmetric positions with respect to the vertical axis, and thereby the peak positions for the strained layer determined by the amount of strain are obtained.

In the case that two peaks for the respective diffraction planes of the single crystal substrate are not located at the symmetric positions as described above, its cause is declination of the axis setting in measuring of the respective diffraction plane. Therefore, in order that the peak of the single crystal substrate for any one of the asymmetric diffraction planes is located at the symmetric position to the peak of the single crystal substrate for the other of the asymmetric diffraction planes, at least the peak position for the strained layer for the said other asymmetric diffraction plane is moved in parallel, and then the peak positions for the strained layer determined by the amount of strain can be obtained by performing modification by the rotational movement.

And, as the single crystal substrate, a silicon single crystal can be used.

The present invention can be applied independently of the type of the single crystal substrate. As the single crystal substrate, a most-used silicon single crystal can be used.

Moreover, the amount of strain to be measured can be a lattice relaxation rate of a SiGe layer and/or a strain rate of a strained silicon layer.

As described above, if the formed strained layer is a SiGe layer, a lattice relaxation rate thereof can be measured. And, if it is a strained silicon layer, a strain rate thereof can be measured. Moreover, even if both a SiGe layer and a strained silicon layer are formed as the strained layer, the respective strained amounts, namely a lattice relaxation rate and a strain rate, can be measured at the same time.

Moreover, it is preferable that the diffraction plane index (XYZ) is (113) or (224).

The diffraction plane to be used here may be any diffraction plane as long as being asymmetrically diffractive and diffraction strength peaks can be obtained. If X-ray diffraction is performed so that the diffraction plane index (XYZ) is (113) or (224), diffraction strength peaks for asymmetric diffraction can be obtained at a sufficient strength.

And, it is possible that when the lattice relaxation rate is calculated, peak positions for the SiGe layer in which the lattice relaxation rate becomes 0% and 100% are calculated from the rotated and modified peak positions for the SiGe layer, and the lattice relaxation rate can be calculated by using the calculated peak positions.

Because peak positions for the SiGe layer in which the lattice relaxation rate becomes 0% and 100% can be easily calculated from the rotated and modified peak positions for the SiGe layer, the respective lattice relaxation rates in the horizontal direction and in the vertical direction can be calculated easily from the relation of these calculated peak positions.

And, it is possible that when the strain rate is calculated, a lattice constant of the strained silicon layer is calculated from the rotated and modified peak positions for the strained silicon layer, and the strain rate is calculated by using the calculated lattice constant.

Because a lattice constant of the strained silicon layer can be calculated easily from the rotated and modified peak positions for the strained silicon layer, the respective strain rates in the horizontal direction and in the vertical direction can be calculated easily from the lattice constant thus calculated and from the normal lattice constant of silicon.

According to the present invention, amounts of strain in the horizontal direction and in the vertical direction can be easily measured in the reciprocal lattice space map obtained from two asymmetric diffraction planes according to X-ray diffraction method. Moreover, measurement of a Tilt angle and a Twist angle are not required in addition, and measurement according to an X-ray diffraction method for creating a reciprocal lattice space map can be accomplished only at the two diffractions of (XYZ) and (−X−YZ). Therefore, measuring can be done in a shorter time and more simply.

BEST MODE FOR CARRYING OUT THE INVENTION

Figure 1:
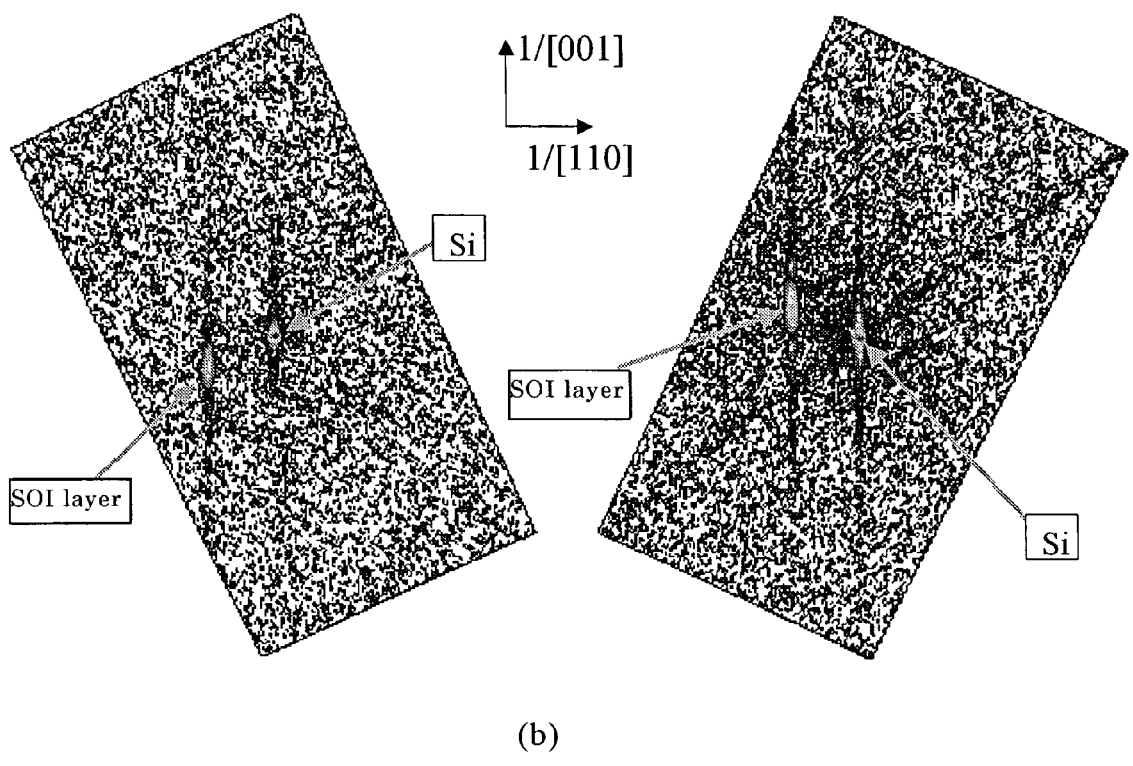
FIG. 1(a) is a section schematic view of a measured SOI wafer, (b) is a reciprocal lattice space map thereof, (c) is a schematic view showing diffraction strength peak positions on the reciprocal lattice space map.
Figure 1:
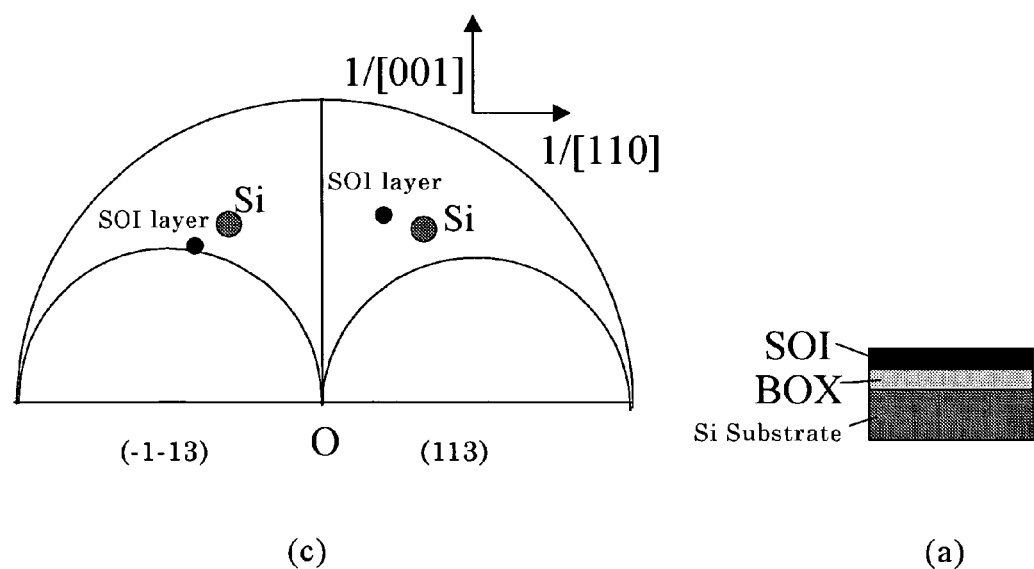

Hereinafter, embodiments of the present invention will be explained. However, the present invention is not limited to these.

Conventionally, in such cases as producing an SGOI wafer by an oxidation-concentration method after epitaxially-growing a SiGe layer on an SOI layer of a bonded SOI wafer, as producing an SGOI wafer by bonding a wafer with a SiGe layer, or as producing according to a bonding method an SSOI wafer with a structure in which a strained Si layer is directly formed on an oxide film, crystal orientation declinations is caused with respect to Twist direction and Tilt direction between the Si substrate and the Strained Si layer or the SiGe layer. There has been a problem that these crystal orientation declinations cause declinations of peak positions for the strained Si layer and the SiGe layer in an X-ray diffraction measurement.

In an X-ray diffraction method, amounts of strain can be obtained from declinations between peak positions of the Si substrate and a strained Si layer and a SiGe layer. However, crystal orientation declination exists in a bonded wafer as described above. Therefore, the effect of position declination due to strain and the effect of position declination due to crystal orientation declination cannot be distinguished. Therefore, it has been difficult to measure according to an X-ray diffraction method amounts of strain of an SGOI wafer and an SSOI wafer which are based on a bonding method.

As a technique for solving this problem, a technique of Extended Abstracts of the 2003 International Conference on Solid State Devices and Materials, Tokyo, 2003, pp. 290-291 as described above has been disclosed. However, there has been a problem that an extremely long time has to be spent on evaluation of a strain amount.

On the other hand, in the case of measuring an amount of strain by micro-Raman spectroscopy, only an amount of strain in the horizontal direction can be measured. In addition, it is required to know Ge concentration in the case of measuring a lattice relaxation rate of a SiGe layer. There has been a problem that a destructive inspection has to be performed for knowing Ge concentration and production yield of wafers is degraded.

Accordingly, the present inventor made repeatedly diligent study and search with respect to a method for measuring an amount of strain accurately by using an X-ray diffraction method with removing effects of declinations of crystal orientations of an SGOI wafer and an SSOI wafer which are based on a bonding method. As a result, it has been found that in the case of measuring an SGOI wafer and an SSOI wafer which are produced by a bonding method according to an X-ray diffraction method with respect to the two of a (XYZ) diffraction plane and a (-X-YZ) diffraction plane which are asymmetric diffraction planes and creating a reciprocal lattice space map from the measured data, effects of position declinations due to crystal orientation declination with respect to peaks of the strained layer appear on the same circumference at the same magnitude in the same direction, and on the other hand, effect of position declination due to strain appears on the same circumference at the same magnitude in the reverse direction. And, it has been found that it is impossible to obtain an amount in itself of position declinations due to crystal orientation declination by the measurement, however, only the effect of position declination due to strain can be separated by using properties of declinations as described above.

And, the present inventor has performed experiment and investigation as described below in which a reciprocal lattice space map of a bonded SOI wafer with no strain is measured by using an X-ray diffraction method with respect to a (XYZ) diffraction plane and a (-X-YZ) diffraction plane which are asymmetric diffraction planes and thereby to confirm that effects of position declinations due to crystal orientation declinations appear on the same circumference at the same magnitude in the same direction on the reciprocal lattice space map.

(Experiment 1)

By using two silicon single crystal wafers with a 200 mm diameter, p-type, and crystal orientation of <100>, there is prepared a bonded SOI wafer based on a Si substrate which has a 110-nm thickness of an SOI layer and a 200-nm thickness of a buried oxide film layer (Buried Oxide, hereinafter, referred to as a BOX layer) and which is produced according to smart cut (a registered trademark) method. And measurement of a reciprocal lattice space map of a (113) diffraction plane and a (-1-13) diffraction plane was performed by an X-ray diffraction apparatus (manufactured by Philips Co. Ltd.).

FIG. 1(a) is a section schematic view of the measured SOI wafer. (b) is a reciprocal lattice space map thereof. (c) is a schematic view showing diffraction strength peak positions on the reciprocal lattice space map. In addition, in the reciprocal lattice space map, an axis in the horizontal direction is 1/[110], an axis in the vertical direction is 1/[001]. From the reciprocal lattice space map, peak positions (wave numbers) of the SOI layer and peak positions (wave numbers) of the Si substrate were investigated. On the (113) diffraction plane shown on the right side of the reciprocal lattice space map, the coordinates of the peak position of the SOI layer was ($2577 \times 10^4$ $cm^{-1}$, $5536 \times 10^4$ $cm^{-1}$), and the coordinates of the peak position of the Si substrate was ($2622 \times 10^4$ $cm^{-1}$, $5516 \times 10^4$ $cm^1$). And, on the (-1-13) diffraction plane shown on the left side of the reciprocal lattice space map, the coordinates of the peak position of the SOI layer was ($-2629 \times 10^4$ $cm^{-1}$, $5512 \times 10^4$ $cm^{-1}$), and the coordinates of the peak position of the Si substrate was ($-2584 \times 10^4$ $cm^{-1}$, $5533 \times 10^4$ $cm^1$). Peak positions of the Si substrate for the respective diffraction planes were not located at symmetric positions with respect to 1/[001] axis. However, the relation of peak positions for the Si substrate and the SOI layer in the respective diffraction planes was that the SOI layer peak was displaced counterclockwise on almost the same circumference from the peak position for the Si substrate with respect to both of the planes, and in addition, the absolute values of X and Y coordinate components of the displacement amounts correspond approximately to each other. And, it was found that they were $45 \times 10^4$ $cm^{-1}$, $20 \times 10^4$ $cm^{-1}$, respectively.

That is, it has been confirmed that effects of position declinations due to crystal orientation declinations appear on the same circumference at the same magnitude in the same direction on the reciprocal lattice space map. The reason why declinations occur on the same circumference as described above is thought that on the reciprocal lattice space map, distances from origin of the diffraction peaks are determined by a reciprocal number of plane intervals of the crystal lattice plane and the lattice plane intervals are not changed by crystal orientation declination, and therefore, the distances from origin of diffraction peaks are not changed by the crystal orientation declination.

The reason why the two peak positions for the Si substrate are not located at symmetric positions with respect to the 1/[001] axis is thought that because the axis setting with respect to a measuring diffraction plane is performed at every measuring of the respective diffraction planes, declination of the axis setting leads to declination of origins of the reciprocal lattice space maps on the respective diffraction planes, therefore peak positions inherently appearing at symmetric positions did not appear at symmetric positions. However, with respect to each diffraction plane of them, the direction, and the amount of displacement of the SOI layer peak position with respect to that of the Si substrate are the same. Therefore, it has been found that, for example, in the case of using the Si substrate peak position for the (113) diffraction plane as the basis, it is possible to transfer the origin in parallel so that the position of the Si substrate peak for the (-1-13) diffraction plane is located at the symmetric position with respect to the 1/[001] axis to correct the position declination due to declination of the axis setting. In this case, each diffraction plane can be used as the basis, the Si substrate peak position for the (−1−13) diffraction plane can also be used as the basis.

Next, the present inventor has performed experiment and investigation as described below in which a reciprocal lattice space map of a SGOI wafer produced by using a SIMOX method, which has no crystal orientation declination caused by bonding is measured by using an X-ray diffraction method with respect to a (XYZ) diffraction plane and a (−X−YZ) diffraction plane which are asymmetric diffraction planes and thereby to confirm that effects of position declinations due to strain appear on the same circumference at the same amount in the reverse direction on the reciprocal lattice space map.

(Experiment 2)

By using silicon single crystal wafers with a 200 mm diameter, p-type, and crystal orientation of <100>, an SGOI wafer (strained Si/SiGe/BOX/Si substrate) with a 20% Ge concentration of a SiGe layer, a 40-nm thickness of the SiGe layer, and a 150-nm thickness of a BOX layer was produced according to a SIMOX method and an oxidation-concentration method. And measurement of reciprocal lattice space maps of a (113) diffraction plane and a (−1−13) diffraction plane was performed with X-ray diffraction apparatus in the same manner as Experiment 1.

Figure 2:
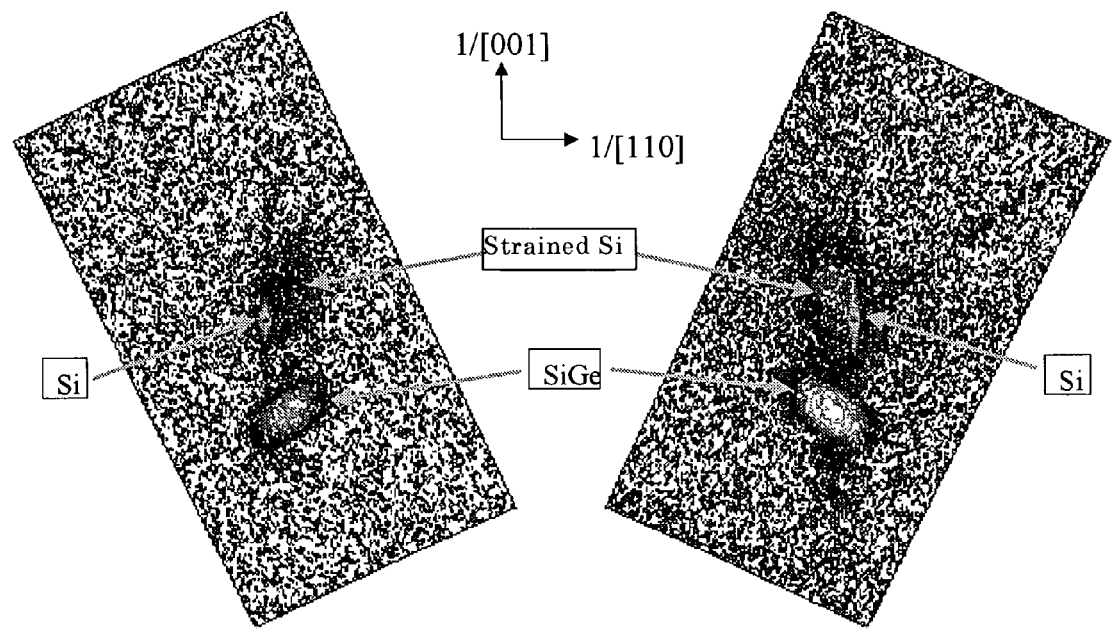
FIG. 2(a) is a section schematic view of an SGOI wafer, (b) is a reciprocal lattice space map thereof, (c) is a schematic view showing peak positions on the reciprocal lattice space map.
Figure 2:
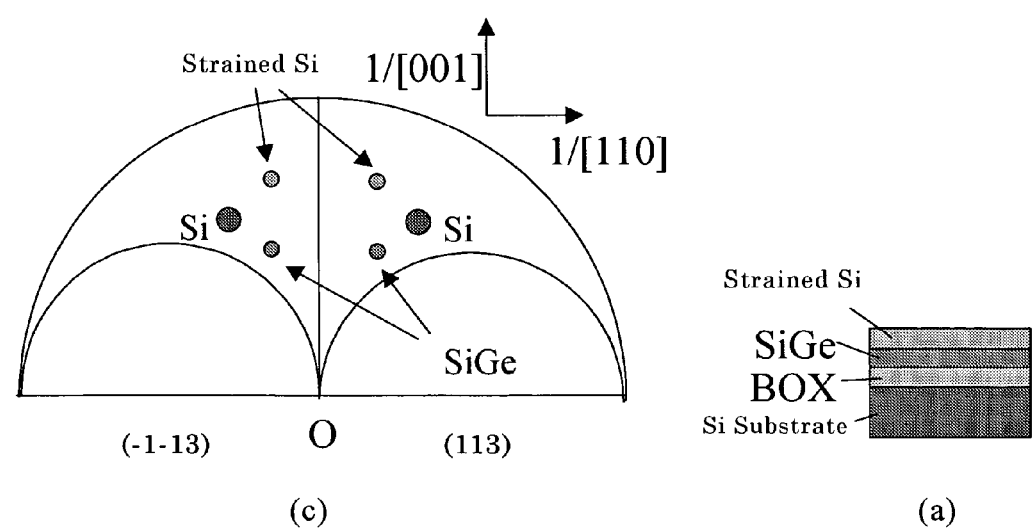
Figure 2:
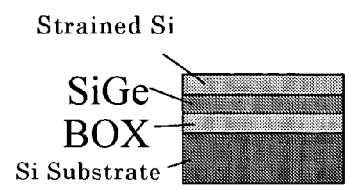

FIG. 2($a$) is a section schematic view of an SGOI wafer. (b) is a reciprocal lattice space map thereof. (c) is a schematic view showing peak positions on the reciprocal lattice space map. In addition, an axis in the horizontal direction of the reciprocal space map is 1/[110], an axis in the vertical direction thereof is 1/[001]. From the reciprocal lattice space map, peak positions for the SiGe layer and peak positions for the Si substrate were investigated. The coordinates of the peak position of the SiGe layer for the (113) diffraction plane shown on the right side of the reciprocal lattice space map was (2587× $10^4$ cm$^{-1}$, 5459×$10^4$ cm$^{-1}$), and the coordinates of the peak position of the Si substrate thereof was (2602×$10^4$ cm$^{-1}$, 5525×$10^4$ cm$^{-1}$). And, the coordinates of the peak position of the SiGe layer of the (−1−13) diffraction plane shown on the left side of the reciprocal lattice space map was (−2586×$10^4$ cm$^{-1}$, 5458×$10^4$ cm$^{-1}$), and the coordinates of the peak position of the Si substrate thereof was (−2603×$10^4$ cm$^{-1}$, 5524× $10^4$ cm$^{-1}$). Because the peak positions for the Si substrate on the reciprocal lattice space map on the respective diffraction planes were at the symmetric positions with respect to a 1/[001] axis as being different from Experiment 1, it is thought that setting of axes when the respective diffraction planes are measured does not decline and the origins on the reciprocal lattice space maps in the respective diffraction planes correspond to each other. And, the relation of peak positions for the Si substrate and the SGOI layer for the respective diffraction planes was that the respective Y coordinates thereof were displaced in the same direction at almost the same magnitude, namely by about −66×$10^4$ cm$^{-1}$. On the other hand, it was found that the X coordinates thereof were displaced in the reverse direction at almost the same magnitude, namely by −15×$10^4$ cm$^{-1}$ in the (113) diffraction plane and by +17×$10^4$ cm$^{-1}$ in the (−1−13) diffraction plane.

That is, it was possible to confirm that effects of position declination due to strain appear on the same circumference at the same magnitude in the reverse direction on the reciprocal lattice space map.

Based on the results of the Experiments and investigations as described above, the present inventor made repeatedly diligent study with respect to strained Si and SiGe wafers which are based on a bonding method, and accomplished the present invention.

That is, a method of the present invention for measuring an amount of strain of a bonded strained wafer (a strain rate or a lattice relaxation rate) in which at least one strained layer such as a strained Si layer or a SiGe layer is formed on a single crystal substrate by a bonding method has characteristics for measuring the bonded strained wafer with respect to two asymmetric diffraction planes with diffraction plane indices (XYZ) and (−X−YZ) by an X-ray diffraction method, creating a reciprocal lattice space map, using that effects of displacements of peak positions due to crystal orientation declinations appear on the same circumference at the same magnitude in the same direction on the reciprocal lattice space map and on the other hand effects of displacements of peak positions due to strain appear on the same circumference at the same magnitude in the reverse direction, therewith separating the effects of position declinations due to crystal orientation declinations from the effects of position declinations due to strain, and thereby being capable of measuring accurately amounts of strain in the horizontal direction and in the vertical direction, namely a strain rate of a strained Si layer or a lattice relaxation rate of a SiGe layer.

Hereinafter, according to a method for measuring an amount of strain of the present invention, the case of measuring a lattice relaxation rate of a relaxed SiGe layer of an SGOI wafer and a strain rate of a strained Si layer which are produced by using a bonding method with using silicon single crystal substrates for (113) and (−1−13) diffraction planes as asymmetric diffraction planes will be exemplified and explained in detail with reference to drawings. However, the present invention is not limited to these.

Figure 3:
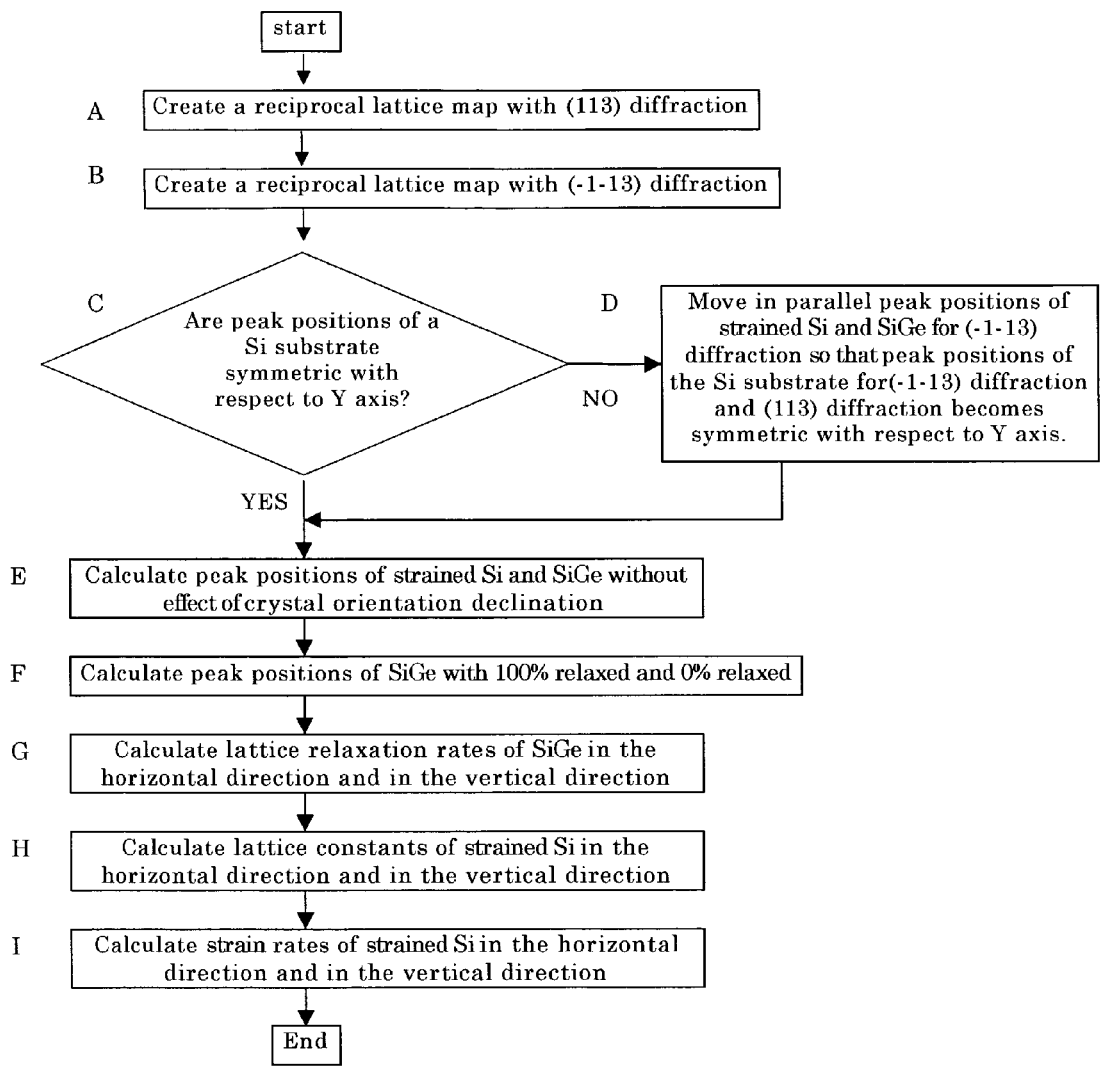
FIG. 3 is a step flow chart showing an example of a method for measuring an amount of strain according to the present invention.

FIG. 3 is a step flow chart showing an example of a method for measuring an amount of strain according to the present invention.

First, as samples for measuring the lattice relaxation rate of a SiGe layer and the strain rate of a strained Si layer, such samples as follows are used. First, a SiGe layer is formed at a 20-% Ge concentration at a 40-nm thickness on an SOI layer of a bonded SOI wafer produced by smart cut (a registered trademark) method. Then, as a oxidation-concentration step, Ge is diffused into the SOI layer with performing dry-oxidation at a temperature of 1000° C. or more, therewith the SOI layer (which becomes a SiGe layer after the oxidation-concentration step) is thinned, then an oxide film on its surface is removed by using a HF solution, and thereby a SiGe layer having a 20-% Ge concentration and a 40-nm thickness on a BOX layer is formed. And, a strained Si layer is epitaxially grown thereon at a 15-nm thickness.

Figure 4:
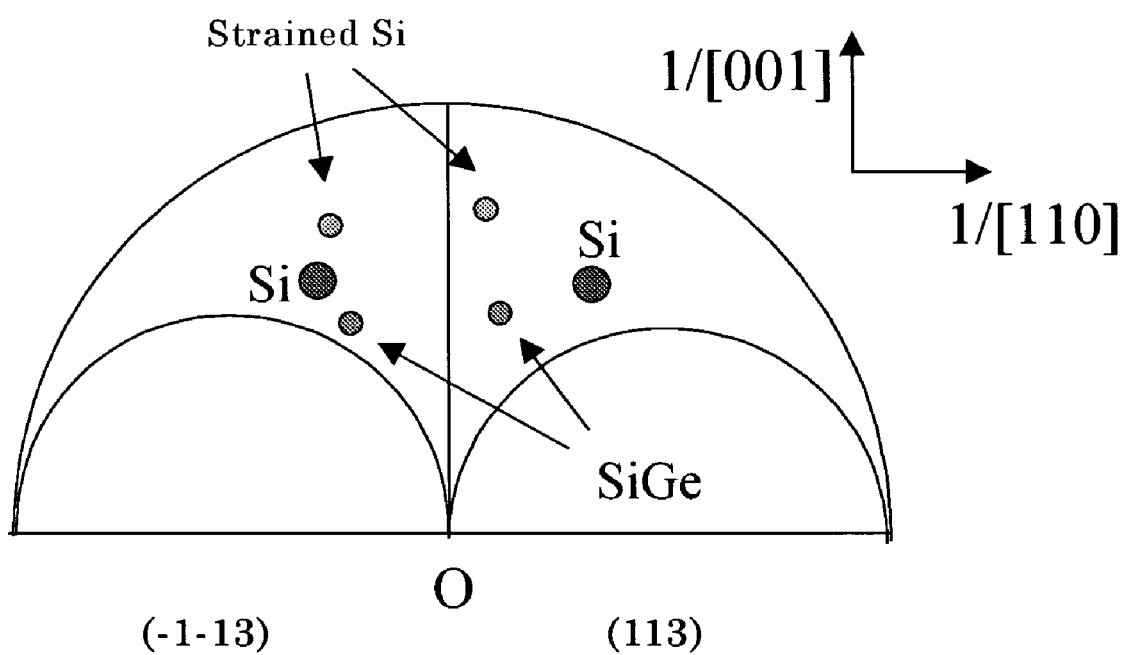
FIG. 4 is a schematic view of a reciprocal lattice space map that is created after measuring samples with respect to two asymmetric diffraction planes with diffraction plane indices (113) and (−1−13) according to an X-ray diffraction method.

The above samples are measured with respect to the two asymmetric diffraction planes of diffraction plane indices (113) and (−1−13) by an X-ray diffraction method, and a reciprocal lattice space map is created from the measured data (FIG. 3A, B). A schematic view of the created reciprocal lattice space map is shown in FIG. 4. The horizontal axis (X axis) is 1/[110] and the vertical axis (Y axis) is 1/[001]. The peak of a diffraction signal for the (113) diffraction plane appears on the positive side of the X axis, and the peak of a diffraction signal for the (−1−13) diffraction plane appears on the negative side thereof.

Next, it is confirmed whether the two peaks for the respective diffraction planes of the Si substrate appearing on the reciprocal lattice space map are located at symmetric positions with respect to the Y axis (FIG. 3C). In this case, because the two peaks are located at symmetric positions with respect to the Y axis, proceed to the next step.

However, in the case that they are not located at symmetric positions with respect to the Y axis, the axis setting is declined in the measurement by an X-ray diffraction and the origins are declined. Therefore, in order that the peak of the Si substrate for one diffraction plane, such as the (113) diffraction plane, is located at the symmetric position to the peak of the Si substrate for the (−1−13) diffraction plane, which is the other diffraction plane, the peaks for the Si substrate, the peaks for the strained Si layer and the SiGe layer for the (−1−13) diffraction plane are moved in parallel (FIG. 3D). However, in the following steps, the peak for the Si substrate for the (−1−13) diffraction plane is not used, therefore it is not necessary to move the peak actually.

The peaks for the SiGe layer and the strained Si layer are located in positions declined from the peak positions for the Si substrate with effects of crystal orientation declination due to Tilt, Twist, or the like and with effects of strain. With respect to the position declination with the effects of strain, strain in the horizontal direction, namely in [110] direction, appears as a position declination in the X axis direction. Strain in the vertical direction, namely in [001] direction, appears as a position declination in the Y axis direction. And, in both directions, if a lattice constant increases by extending of crystal lattice, plane intervals become large and therefore position declination occurs to the negative direction on the reciprocal lattice space map, and if the lattice constant decreases by shrinking of crystal lattice, position declination occurs to the positive direction on the reciprocal space map.

Next, the peak positions for the SiGe layer and the strained Si layer are moved rotationally and modified in the circumferential direction as centering the origin O so that the two peak positions of the same strained layer for the respective diffraction planes appearing on the reciprocal lattice space map are located at symmetric positions with respect to the Y axis. Hereinafter, the rotation and modification method is specifically explained by exemplifying peaks for the SiGe layer.

Figure 5:
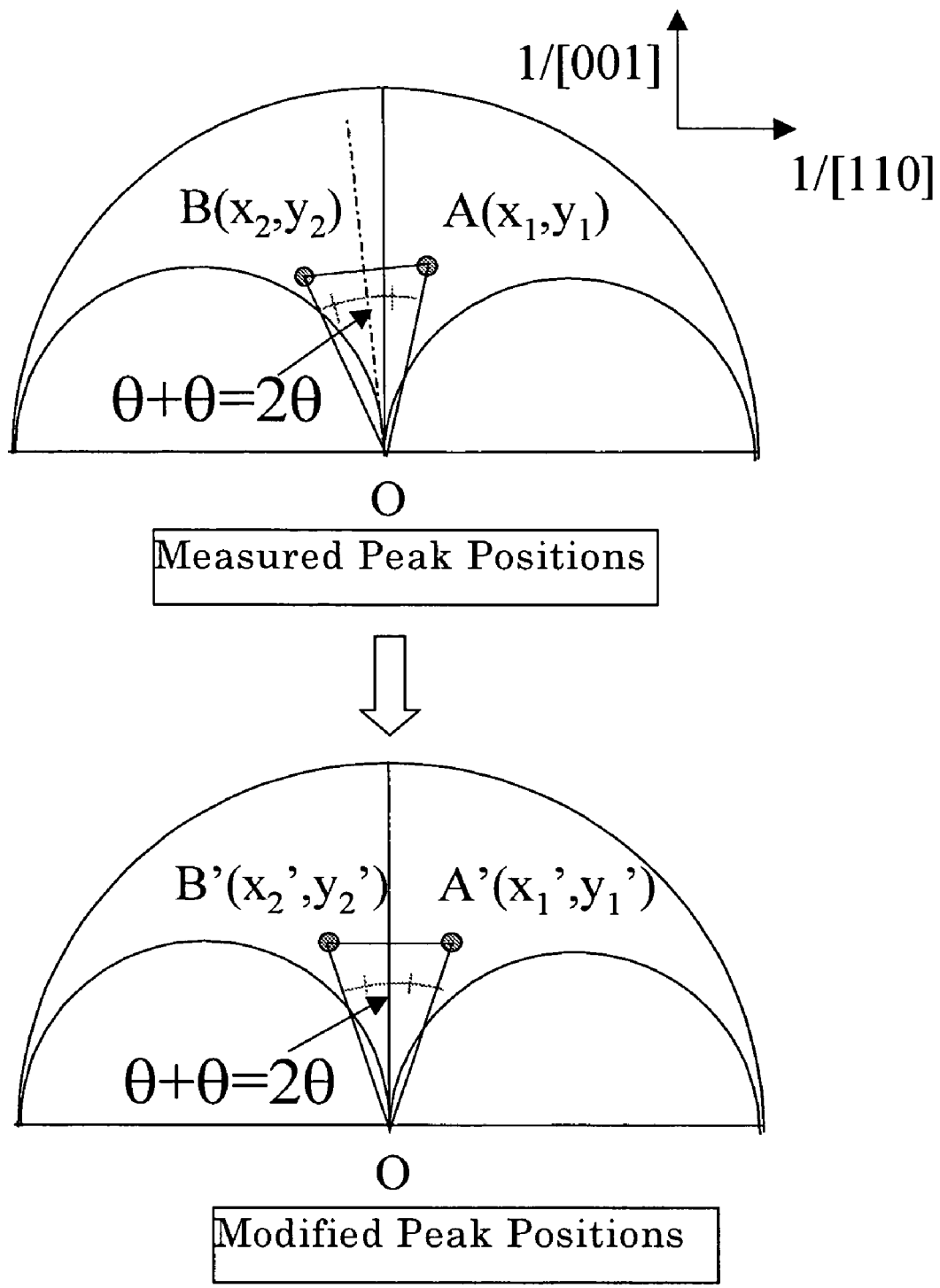
FIG. 5 is an explanation view for explaining a method for rotating and modifying peaks of a SiGe layer.

FIG. 5 is an explanation view for explaining a method for rotating and modifying peaks of the SiGe layer.

First, on the reciprocal lattice space map, when the peak positions measured (or moved in parallel after the measurement) of the SiGe layer for the (113) and (−1−13) diffraction planes are represented as $A(x_1, y_1)$ and $B(x_2, y_2)$ respectively and an angle between OA and OB is represented as $2\theta$, the A and B exist on the same circumference according to the described reason. Because the A and B exist on the same circumference as described above, the distances from the origin O are the same;

$$OA=(x_1^2+y_1^2)^{1/2}=(x_2^2+y_2^2)^{1/2}=OB,$$

$$AB=[(x_1-x_2)^2+(y_1-y_2)^2]^{1/2}$$

and;

$$AB^2=OA^2+OB^2-2OA \cdot OB \cos 2\theta$$

therefore;

$$\cos 2\theta=(x_1x_2+y_1y_2)/(x_1^2+y_1^2).$$

Moreover, the A and B are defined to become $A'(x_1', y_1')$ and $B'(x_2', y2')$ respectively after the rotational movement. After the rotational movement, A' and B' are located at symmetric positions with respect to the Y axis. Therefore, both an angle between OA' and the Y axis and an angle between OB' and the Y axis become $\theta$. Moreover, $$OA'=OB'=OA$$

and;

$$\sin \theta[(1-\cos 2\theta)/2]^{1/2},$$

$$\cos \theta=[(1+\cos 2\theta)/2]^{1/2}$$

therefore;

$$x_1'=-x_2'=(x_1^2+y_1^2)^{1/2} \sin \theta=[(x_1(x_1-x_2)+y_1(y_1-y_2))/2]^{1/2},$$

$$y_1'=y_2'=(x_1^2+y_1^2)^{1/2} \cos \theta=[(x_1(x_1+x_2)+y_1(y_1+y_2))/2]^{1/2}.$$

As described above, the rotationally moved and modified peak positions for the SiGe layer can be obtained (FIG. 3E). The peak positions for the SiGe layer modified as described above are peak positions determined by a lattice relaxation rate of the SiGe layer with removing position declination due to crystal orientation declination caused by Tilt, Twist, or the like of the wafer. In addition, the peaks for the strained Si layer are rotated and modified by the same method.

Next, a lattice relaxation rate is obtained from the peak positions for the SiGe layer modified as described above (FIG. 3G). When a lattice relaxation rate is calculated, peak positions for the SiGe layer in which the lattice relaxation rate becomes 0% and 100% are calculated from the modified peak positions for the SiGe layer (FIG. 3F), and a lattice relaxation rate can be calculated by using the calculated peak positions. An example of the specific method is presented as follows. In addition, a lattice relaxation rate can be obtained from a peak of the SiGe layer for any diffraction plane. However, here, the case of obtaining a lattice relaxation rate from a peak position of the SiGe layer for the (113) diffraction plane will be presented.

Figure 6:
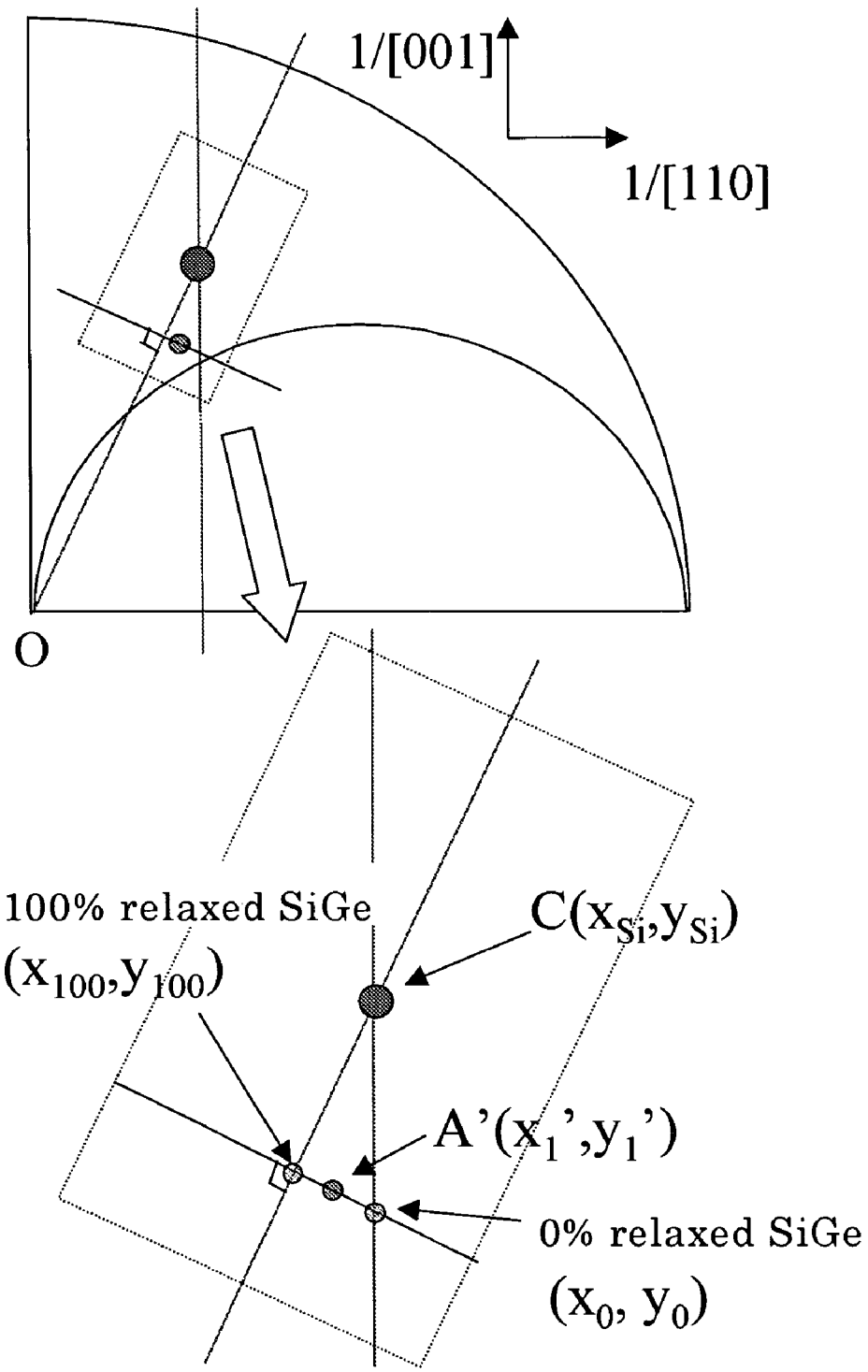
FIG. 6 is an explanation view for explaining an example of a method for obtaining a lattice relaxation rate of a SiGe layer.

FIG. 6 is an explanation view for explaining an example of a method for obtaining a lattice relaxation rate of the SiGe layer. The rotationally moved and modified peak of the SiGe layer is represented as $A'(x_1', y_1')$, and the peak of the Si substrate is represented as $C(x_{Si}, y_{Si})$ First, a straight line $l_1$ passing through the origin O and the C is represented as;

$$l_1: y=(y_{Si}/x_{Si})x.$$

Next, a straight line $l_2$ passing through the A' with vertical to the straight line $l_1$ is represented as;

$$l_2: y=-(x_{Si}/y_{Si})(x-x_1')+y_1'$$

The peak position for the SiGe layer in which a lattice relaxation rate becomes 100% can be obtained as the intersection point of the straight lines $l_1$ and $l_2$ because its crystal orientation is the same as Si. That is, the coordinates are represented as $(x_{100}, y_{100})$;

$$x_{100}=(x_{Si}^2 x_1'+x_{Si}y_{Si}y_1')/(x_{Si}^2+y_{Si}^2),$$

$$y_{100}=(x_{Si}y_{Si}x_1'+y_{Si}^2 y_1')/(x_{Si}^2+y_{Si}^2).$$

On the other hand, the peak position of the SiGe layer in which a lattice relaxation rate becomes 0% can be obtained with $x=x_{Si}$ in the straight line $l_2$ because the lattice constant in the horizontal direction is equal to the lattice constant of Si. That is, in the case that the coordinates are represented as $(x_0, y_0)$;

$$x_0=x_{Si}$$

$$y_0=-(x_{Si}/y_{Si})(x_{Si}-x_1')+y_1'.$$

A lattice relaxation rate $R_{hor}$ in the horizontal direction and a lattice relaxation rate $R_{ver}$ in the vertical direction are obtained as relative positions for the rotated and modified peak position with respect to the peak positions for the SiGe layer in which a lattice relaxation rate becomes 0% and 100%. That is;

$$R_{hor}=(x_0-x_1)/(x_0-x_{100}) \times 100 [\%],$$

$R_{ver}=(y_1'-y_0)/(y_{100}-y_0)\times 100[\%]$.

As explained above, according to the present invention, it is possible to make a reciprocal lattice space map with respect to the two asymmetric diffraction planes with diffraction plane indices (113) and (−1−13) by an X-ray diffraction method and to calculate a lattice relaxation rate of the SiGe layer from the peak positions for the respective diffraction planes of the Si substrate and the SiGe layer on the reciprocal lattice space map.

Next, a strain rate is obtained from the peak positions for the strained Si layer moved rotationally and modified by the same method as the SiGe layer (FIG. 3I). When a strain rate is calculated, a lattice constant for the strained silicon layer is calculated from the modified peak positions for the strained Si layer (FIG. 3H), and thereby a strain rate can be obtained by using thus calculated lattice constant. An example of the specific method is presented as follows. In addition, a strain rate can be obtained from a peak for the strained Si layer for any diffraction plane. However, here, the case of obtaining a strain rate from a peak position of the strained Si layer for the (113) diffraction plane will be presented.

Figure 7:
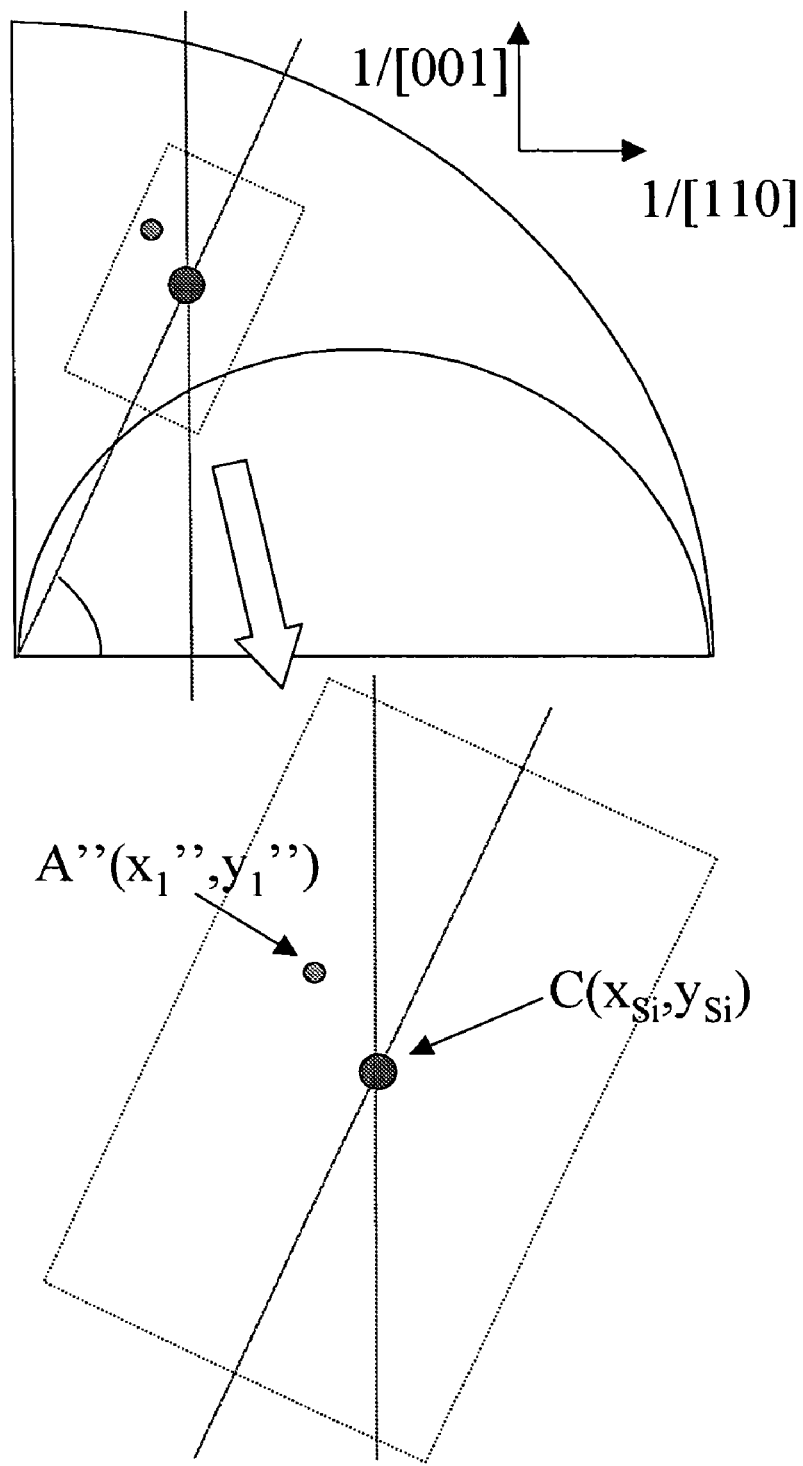
FIG. 7 is an explanation view for explaining an example of a method for obtaining a strain rate of a strained Si layer.
Figure 8:
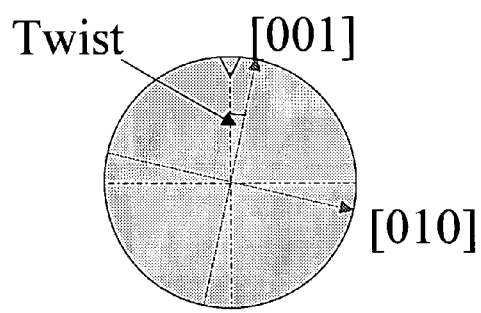
FIG. 8 is an explanation view showing crystal orientation declination caused in a wafer with a crystal plane orientation of (100), (a) is a view seeing a wafer from a direction vertical to a surface thereof, (b) is a view seeing a wafer from a direction parallel to a surface thereof.
Figure 8:
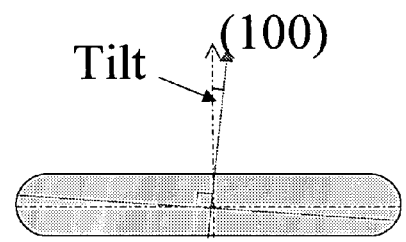
Figure 9:
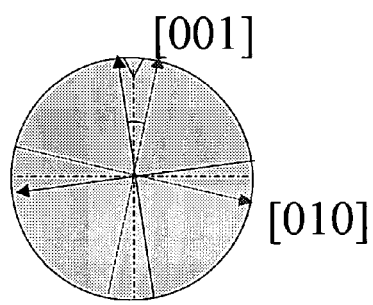
FIG. 9 is a schematic view showing crystal orientation declination to be generated in a bonded wafer produced by bonding two Si wafers with crystal plane orientation (100) with one of the wafer being for forming an SOI layer and with the other being for a supporting substrate. (a) is a view seeing a wafer from a direction vertical to a surface thereof, (b) is a view seeing a wafer from a direction parallel to a surface thereof.
Figure 9:
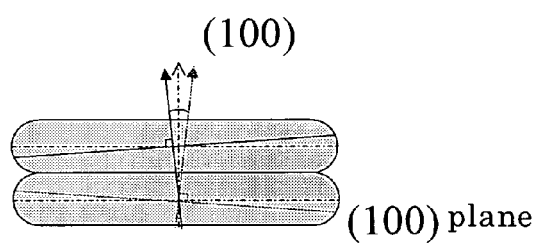

FIG. 7 is an explanation view for explaining an example of a method for obtaining a strain rate of a strained Si layer. The rotationally moved and modified peak position for the strained Si layer is represented as A″ ($x_1''$, $y_1''$).

In general, plane intervals $d_{hkl}$ of a crystal plane with a Miller index (hkl) in a crystal with lattice constant a are represented as;

$d_{hkl}=a/(h^2+k^2+l^2)^{1/2}$.

From the relation between the coordinates on the reciprocal lattice space map and the plane intervals;

$d_{hk0}=1/x_1''$, $d_{001}=1/y_1''$.

Therefore, lattice constants $a_{hor}$ and $a_{ver}$ in the horizontal direction and in the vertical direction of the strained Si layer are;

$a_{hor}=(h^2+k^2)^{1/2}/x_1''$, $a_{ver}=1/y_1''$.

Therefore, strain rates $\epsilon_{hor}$ and $\epsilon_{ver}$ in the horizontal direction and in the vertical direction of the strained Si layer are, on the basis of a lattice constant $a_{Si}$(5.43 Å) of silicon;

$\epsilon_{hor}=(a_{Si}-a_{hor})/a_{Si}\times 100[\%]$, $\epsilon_{ver}=(a_{Si}-a_{ver})/a_{Si}\times 100[\%]$.

As explained above, according to the present invention, a reciprocal lattice space map is created with respect to two asymmetric diffraction planes with diffraction plane indices (113) and (−1−13) by an X-ray diffraction method, and a strain rate of the strained Si layer can be calculated from peak positions for the respective diffraction planes of a Si substrate and a strained Si layer on the reciprocal lattice space map.

Hereinafter, the present invention is specifically explained according to Examples of the present invention. However, the present invention is not limited to these.

EXAMPLE 1

As a sample 1 for measuring a lattice relaxation rate of a SiGe layer, production of an SGOI wafer using the oxidation-concentration method was performed. On a bonded SOI wafer with a 200-mm diameter produced by smart cut (a registered trademark) method, a SiGe layer was produced at a 20-% Ge concentration at a 40-nm thickness, and then Ge was diffused into the SOI layer by performing dry-oxidation at a temperature of 1000° C. or more, and therewith the SOI layer (which becomes a SiGe layer after the oxidation-concentration step) was thinned, then an oxide film on its surface is removed by using a HF solution, and thereby forming a SiGe layer with a 20-% Ge concentration and a 40-nm thickness on a BOX layer. At this time, the object was to measure a lattice relaxation rate of the SiGe layer, therefore, a strained Si layer was not formed on the SiGe layer.

And, measurement of a reciprocal lattice space map of a (113) diffraction plane and a (−1−13) diffraction plane was performed by an X-ray diffraction apparatus (manufactured by Philips Co. Ltd.). And, according to the above-described steps, a lattice relaxation rate of the SiGe layer was obtained. The two peaks of the Si substrate for the (113) and (−1−1−3) diffraction planes obtained by the measurement were located at symmetric positions with respect to the Y axis. Therefore, peak positions for the SiGe layer were not moved in parallel but moved rotationally and modified, thereby peak positions in which effect of declination due to the crystal orientation was removed was given. And, peak positions for the SiGe layer in which a lattice relaxation rate is 100% and 0% were obtained. From the relation of relative position to these, lattice relaxation rates in the horizontal direction and in the vertical direction were obtained. As a result, the lattice relaxation rates were 84.91% in both directions. These results were summarized in Table 1.

TABLE 1

| | (113) Diffraction Plane | (−1-13) Diffraction Plane |
|---|---|---|
| Measured Peak Position | Si (2603 × 10⁴ cm⁻¹, 5525 × 10⁴ cm⁻¹) SiGe (2533 × 10⁴ cm⁻¹, 5484 × 10⁴ cm⁻¹) | Si (−2602 × 10⁴ cm⁻¹, 5525 × 10⁴ cm⁻¹) SiGe (−2625 × 10⁴ cm⁻¹, 5441 × 10⁴ cm⁻¹) |
| Modified Peak Position | SiGe (2579 × 10⁴ cm⁻¹, 5463 × 10⁴ cm⁻¹) | — |
| Peak Positions of a SiGe Layer with A Lattice Relaxation Rate of 100% or 0% | 100% (2574 × 10⁴ cm⁻¹, 5464 × 10⁴ cm⁻¹) 0% (2603 × 10⁴ cm⁻¹, 5451 × 10⁴ cm⁻¹) | — |
| Lattice Relaxation Rate | $R_{hor}$: 84.91%, $R_{ver}$: 84.91% | |

EXAMPLE 2

As a sample 2 for measuring a strain rate of a strained Si layer, production of an SGOI wafer was performed. On a bonded SOI wafer with a 200-mm diameter produced by smart cut (a registered trademark) method, a SiGe layer was formed at a 20-% Ge concentration at a 40-nm thickness, and then Ge was diffused into the SOI layer by performing dry-oxidation at a temperature of 1000° C. or more, and therewith the SOI layer (which becomes a SiGe layer after the oxidation-concentration step) was thinned, then an oxide film on its surface was removed by using a HF solution, and thereby forming a SiGe layer with a 20-% Ge concentration and a 40-nm thickness on a BOX layer. And then, a Si layer was epitaxially grown on the SiGe layer by a thickness of 50 nm to gain a strained Si layer.

And, measurement of a reciprocal lattice space map of a (113) diffraction plane and a (−1−13) diffraction plane was performed with an X-ray diffraction apparatus (manufactured by Philips Co. Ltd.). And, according to the above-described steps, a strain rate of the strained Si layer was obtained. In this case, the two peaks of the Si substrate for the (113) and (−1−13) diffraction planes obtained by the measurement were located at symmetric positions with respect to the Y axis. Therefore, peak positions for the strained Si layer were not moved in parallel but moved rotationally and modified, thereby a peak position in which effect of declination due to the crystal orientation was removed was given. And, a lattice constant of the strained Si layer was obtained, and a strain rate in the horizontal direction and in the vertical direction was obtained from a normal lattice constant of silicon. As a result, a strain rate in the horizontal direction was −1.065% and a strain rate in the vertical direction was 1.198%. These results were summarized in Table 2.

TABLE 2

|  | (113) Diffraction Plane | (−1−13) Diffraction Plane |
|---|---|---|
| Measured Peak Position | Si (2603 × 10$^4$ cm$^{-1}$, 5525 × 10$^4$ cm$^{-1}$) Strained Si (2530 × 10$^4$ cm$^{-1}$, 5613 × 10$^4$ cm$^{-1}$) | Si (−2602 × 10$^4$ cm$^{-1}$, 5525 × 10$^4$ cm$^{-1}$) Strained Si (−2624 × 10$^4$ cm$^{-1}$, 5570 × 10$^4$ cm$^{-1}$) |
| Modified Peak Position | Strained Si (2577 × 10$^4$ cm$^{-1}$, 5592 × 10$^4$ cm$^{-1}$) | — |
| Lattice constants of strained Si layer in the horizontal direction and in the vertical direction | $a_{hor}$ (5.488 Å) $a_{ver}$ (5.365 Å) | — |
| Strain Rate | $\epsilon_{hor}$: −1.065%, $\epsilon_{ver}$: 1.198% | |

In addition, the present invention is not limited to the embodiments described above. The above-described embodiments are merely examples, and those having the substantially same constitution as that described in the appended claims and providing the similar working effects are included in the scope of the present invention.

For example, in the above-described Examples, the asymmetric diffraction plane was the (113) diffraction plane. However, an asymmetric diffraction plane through which diffraction peaks of the substrate and the strained layer can be obtained is suitable, and the (224) diffraction plane can also be used.

Moreover, the case in which the substrate is a silicon substrate and the strained layer is a SiGe layer and a Strained Si layer was described. However, a compound semiconductor such as GaAs can also be used as long as a strained layer is formed on a single crystal substrate by the bonding method.

The invention claimed is:

1. A method for measuring an amount of strain of a bonded strained wafer in which at least one strained layer is formed on a single crystal substrate by a bonding method, wherein at least, the bonded strained wafer is measured with respect to two asymmetric diffraction planes with diffraction plane indices (XYZ) and (−X−YZ) by an X-ray diffraction method, a reciprocal lattice space map is created from the measured data, and the amount of strain of the strained layer is calculated from the peak positions for the respective diffraction planes of the single crystal substrate and the strained layer appearing on the reciprocal lattice space map.

2. The method for measuring an amount of strain according to claim 1, wherein when the amount of strain of the strained layer is calculated, in the case that two peaks for the respective diffraction planes of the single crystal substrate appearing on the reciprocal lattice space map are located at symmetric positions with respect to a vertical axis passing through the origin of the reciprocal lattice space map, the peak positions for the strained layer are moved rotationally and modified in the circumferential direction centering the origin so that the two peak positions for the respective diffraction planes of the same strained layer appearing on the reciprocal lattice space map is located symmetrically with respect to the vertical axis, and thereby the peak positions for the strained layer determined by the amount of strain are obtained.

3. The method for measuring an amount of strain according to claim 2, wherein as the single crystal substrate, a silicon single crystal is used.

4. The method for measuring an amount of strain according to claim 3, wherein the amount of strain to be measured is a lattice relaxation rate of a SiGe layer and/or a strain rate of a strained silicon layer.

5. The method for measuring an amount of strain according to claim 4, wherein the diffraction plane index (XYZ) is (113) or (224).

6. The method for measuring an amount of strain according to claim 4, wherein when the lattice relaxation rate is calculated, peak positions for the SiGe layer in which the lattice relaxation rate becomes 0% and 100% are calculated from the rotated and modified peak positions for the SiGe layer, the lattice relaxation rate is calculated by using the calculated peak positions.

7. The method for measuring an amount of strain according to claim 4, wherein when the strain rate is calculated, a lattice constant of the strained silicon layer is calculated from the rotated and modified peak positions for the strained silicon layer, the strain rate is calculated by using the calculated lattice constant.

8. The method for measuring an amount of strain according to claim 1, wherein in the case that two peaks for the respective diffraction planes of the single crystal substrate are not located at the symmetric positions, in order that the peak of the single crystal substrate for any one of the asymmetric diffraction planes is located at the symmetric position to the peak of the single crystal substrate for the other of the asymmetric diffraction planes, at least the peak position for the strained layer for the said other asymmetric diffraction plane is moved in parallel, and then the peak positions for the strained layer are moved rotationally and modified in the circumferential direction centering the origin so that the two peak positions for the respective diffraction planes of the same strained layer appearing on the reciprocal lattice space map is located symmetrically with respect to the vertical axis, and thereby the peak positions for the strained layer determined by the amount of strain are obtained.

9. The method for measuring an amount of strain according to claim 1, wherein as the single crystal substrate, a silicon single crystal is used.

10. The method for measuring an amount of strain according to claim 9, wherein as the single crystal substrate, a silicon single crystal is used.

11. The method for measuring an amount of strain according to claim 9, wherein the amount of strain to be measured is a lattice relaxation rate of a SiGe layer and/or a strain rate of a strained silicon layer.

12. The method for measuring an amount of strain according to claim 11, wherein the diffraction plane index (XYZ) is (113) or (224).

13. The method for measuring an amount of strain according to claim 11, wherein when the lattice relaxation rate is calculated, peak positions for the SiGe layer in which the lattice relaxation rate becomes 0% and 100% are calculated from the rotated and modified peak positions for the SiGe layer, the lattice relaxation rate is calculated by using the calculated peak positions.

14. The method for measuring an amount of strain according to claim 11, wherein when the strain rate is calculated, a lattice constant of the strained silicon layer is calculated from the rotated and modified peak positions for the strained silicon layer, the strain rate is calculated by using the calculated lattice constant.

15. The method for measuring an amount of strain according to claim 10, wherein the amount of strain to be measured is a lattice relaxation rate of a SiGe layer and/or a strain rate of a strained silicon layer.

16. The method for measuring an amount of strain according to claim 15, wherein when the lattice relaxation rate is calculated, peak positions for the SiGe layer in which the lattice relaxation rate becomes 0% and 100% are calculated from the rotated and modified peak positions for the SiGe layer, the lattice relaxation rate is calculated by using the calculated peak positions.

17. The method for measuring an amount of strain according to claim 15, wherein when the strain rate is calculated, a lattice constant of the strained silicon layer is calculated from the rotated and modified peak positions for the strained silicon layer, the strain rate is calculated by using the calculated lattice constant.

18. The method for measuring an amount of strain according to claim 1, wherein the diffraction plane index (XYZ) is (113) or (224).

* * * * *